United States Patent
Hacimuftuoglu et al.

(10) Patent No.: US 10,758,521 B2
(45) Date of Patent: Sep. 1, 2020

(54) N3,N6-BIS(2-(5-ETHOXY-1H-INDOLE-3-YL)ETHYL)-2,6-DIMETHYL-4-(2-NITROPHENYL)PYRIDINE-3,5-DICARBOXAMIDE AND USE THEREOF IN THE FIELD OF NEUROTOXICITY

(71) Applicants: ATATURK UNIVERSITESI BILIMSEL ARASTIRMA PROJELERI BIRIMI, Erzurum (TR); Ahmet Hacimuftuoglu, Erzurum (TR); Orhan Ates, Istanbul (TR); Nurullah Saracoglu, Erzurum (TR); Ali Taghizadehghalehjoughi, Erzurum (TR); Farrokh Lafzi, Erzurum (TR)

(72) Inventors: Ahmet Hacimuftuoglu, Erzurum (TR); Orhan Ates, Istanbul (TR); Nurullah Saracoglu, Erzurum (TR); Ali Taghizadehghalehjoughi, Erzurum (TR); Farrokh Lafzi, Erzurum (TR)

(*) Notice: Subject to any disclaimer, the term of this patent is extended or adjusted under 35 U.S.C. 154(b) by 0 days.

(21) Appl. No.: 16/435,820

(22) Filed: Jun. 10, 2019

(65) Prior Publication Data
US 2019/0290628 A1    Sep. 26, 2019

Related U.S. Application Data

(62) Division of application No. 16/069,776, filed as application No. PCT/TR2017/050038 on Jan. 26, 2017, now Pat. No. 10,576,072.

(30) Foreign Application Priority Data
Jan. 26, 2016   (TR) .................... 2016/01023

(51) Int. Cl.
C07D 401/14    (2006.01)
A61K 31/4439   (2006.01)

(52) U.S. Cl.
CPC ........ *A61K 31/4439* (2013.01); *C07D 401/14* (2013.01)

(58) Field of Classification Search
CPC .................................................. C07D 401/14
USPC ....................................................... 546/277.4
See application file for complete search history.

(56) References Cited

PUBLICATIONS

Sarma et al., "Corrditination, etc.," J of Molecular Structure, 1052, 197-203. (Year: 2013).*

* cited by examiner

*Primary Examiner* — Patricia L Morris

(57) ABSTRACT

The invention relates to a molecule enabling removal of neurotoxicity observed in neuron cells due to various reasons.

2 Claims, No Drawings

N3,N6-BIS(2-(5-METHOXY-1H-INDOLE-3-YL) ETHYL)-2,6-DIMETHYL-4-(2-NITRO-PHENYL)PYRIDINE-3,5-DICARBOXAMIDE AND USE THEREOF IN THE FIELD OF NEUROTOXICITY

CROSS-REFERENCE TO RELATED U.S. APPLICATIONS

The present application is a division of U.S. application Ser. No. 16/069,776, filed on Jul. 12, 2018, presently pending.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

THE RELATED ART

The invention relates to a molecule enabling removal of neurotoxicity observed in neuron cells due to various reasons.

The invention particularly relates to the $N^3,N^5$-bis(2-(5-methoxy-1H-indole-3-yl)ethyl)-2,6-dimethyl-4-(2-nitrophenyl)pyridine-3,5-dicarboxamide compound obtained by using two different Nifepidine and Melatonin molecules as the starting materials.

THE PRIOR ART

Brain is an organ that is almost impossible to recover functionally following serious neuronal damages. Damaged neurons either die or heal slowly in a certain time depending on the developmental age of the organism, anatomic localization of the cell, and the type, severity, and time period of the damage.

Normally, the glutamate concentration released to the synaptic gap can reach very high levels; but such a high concentration only lasts for a few milliseconds. When this period is extended, neurons are exposed to a killer excitation due to excessive stimulation of neuronal glutamate receptors. As a result of studies researching the effects of hypoxia and cerebral impacts, it was found out that exitotoxicity is responsible for the destruction encountered after cerebral damage. In experimental animal studies, ischemia-related neuronal damage can be prevented via microinjection of glutamate receptor antagonists. It is reported that glutamate antagonists are neuroprotective in stroke and head trauma in rodents and primates. All these results show that; intensive accumulation of glutamate during ischemia stimulates glutamate receptors, which triggers a series of reactions causing neuronal death. It is believed that the reduced oxygen concentration as a result of ischemia prevents energy dependent glutamate re-uptake and thus cause increase in glutamate.

Glaucoma is reported as the worldwide most common reason for irreversible vision loss. It is believed to effect more than fifty million people. While the reason for retina ganglion cell (RGH) loss cannot be understood completely; the major risk factor causing glaucoma is high intraocular pressure. The prior art treatments for glaucoma ensure reduction of intraocular pressure via medicine or surgical techniques. However, pressure-independent loss of field of vision continues in some patients even though the intraocular pressure is reduced. It is known that in glaucomatous optic neuropathy also the process of formation of pathology is multifactorial like in other neurodegenerative diseases, and variable cellular factors play a role in optic neuropathy in molecular level. Any treatment mechanism that delays, protects, or reverses neuron cell death is called as "neuron protection".

Two important situations that cause neuronal damage in case of energy deficiency are disruption of the reabsorption of excitatory amino acid glutamate that is released to the synaptic gap, and the function loss of the sodium-potassium pump required for increase of glutamate in the synaptic gap and maintenance of the membrane potential. Loss of cell membrane potential as well as stimulation of NMDA and AMPA receptors by the glutamate accumulated in the synaptic gap increase sodium and calcium permeability of the cell. As a result intracellular sodium and calcium concentration increase. It is known that permanent brain damage is reduced if the event is stopped at this stage. Most neuroprotective agents used in experimental studies are effective in techniques up to this stage.

The effects of the prior art treatments on glutamate toxicity are limited. Early treatment is essential for these diseases and the prior art treatments extend the treatment period. This negatively affects the progression of disease.

As a result, the above said drawbacks and the inadequacy of the prior art solutions about the subject have necessitated an improvement in the technical field related to compounds eliminating neurotoxicity observed in neuron cells due to various reasons.

Purpose of the Invention

The invention relates to a molecule for eliminating neurotoxicity observed in neuron cells due to various reasons, which meets the above said requirements, eliminates all of the drawbacks, and brings some additional advantages.

The primary purpose of the invention is to be a molecule which eliminates neurotoxicity observed in neuron cells due to various reasons.

A purpose of the invention is to be a specific glutamate blocker.

Another purpose of the invention is to have anti-oxidant characteristics.

Another purpose of the invention is to be a T-type Ca channel blocker.

In order to achieve the above said purposes, the invention comprises $N^3,N^5$-bis(2-(5-methoxy-1H-indole-3-yl)ethyl)-2,6-dimethyl-4-(2-nitrophenyl)pyridine-3,5-dicarboxamide molecule with the below given formulation:

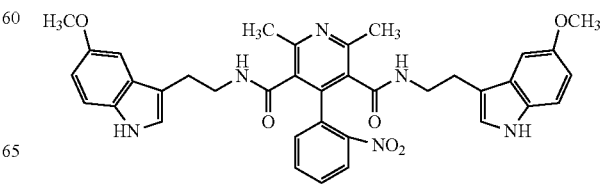

which eliminates neurotoxicity observed in neuron cells.

The structural and characteristic features of the invention and all of its advantages shall be understood better with the figures and the detailed description given below in reference to the figures, and therefore, the assessment should be made by taking into account the said figures and detailed explanations.

DETAILED DESCRIPTION OF THE INVENTION

In this detailed description, the preferred embodiments of a molecule for eliminating neurotoxicity observed in neuron cells due to various reasons, according to the invention are only disclosed for better understanding of the subject without forming any limiting effect.

The invention is a molecule which eliminates neurotoxicity observed in neuron cells due to various reasons. The chemical compound according to the invention is: $N^3,N^5$-bis(2-(5-methoxy-1H-indole-3-yl)ethyl)-2,6-dimethyl-4-(2-nitrophenyl)pyridine-3,5-dicarboxamide.

The molecule according to the invention defines two different functions, since it is formed of combination of two different molecules. Said molecules are: Nifepidine and Melatonin.

Nifepidine is a substance having the structure of calcium-channel blocker dihydropyridine. It selectively inhibits entrance of calcium ions into the cell even at low doses, by being attached to calcium channels.

Melatonin spreads extensively along the organism and enters cellular compartments easily due to its amphophilic and small molecular structure. This natural compound is a strong in vitro and in vivo cytostatic agent with strong antioxidant characteristics.

The Synthesis Method of $N^3,N^5$-bis(2-(5-methoxy-1H-indole-3-yl)ethyl)-2,6-dimethyl-4-(2-nitrophenyl)pyridine-3,5-dicarboxamide Molecule According to the Invention

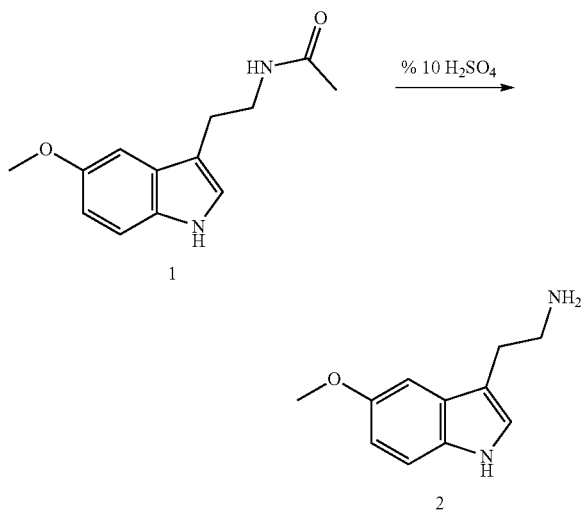

Synthesis of 5-methoxytryptamine (2): Melatonin (1) is used as the starting material of said synthesis.

Melatonin is boiled at 90° C. for 8 hours in a 1 g (4.3 mmol) 40 mL 10% $H_2SO_4$ (sulphuric acid) solution. After the reaction is brought to room temperature, 20% of NaOH (sodium hydroxide) is added until the medium becomes alkaline. Afterwards, it is washed with ethyl acetate (3×20) and the organic phase is dried over $Na_2SO_4$. The solvent is removed under vacuum. 550 mg crude product is obtained (67%) as a yellow solid.

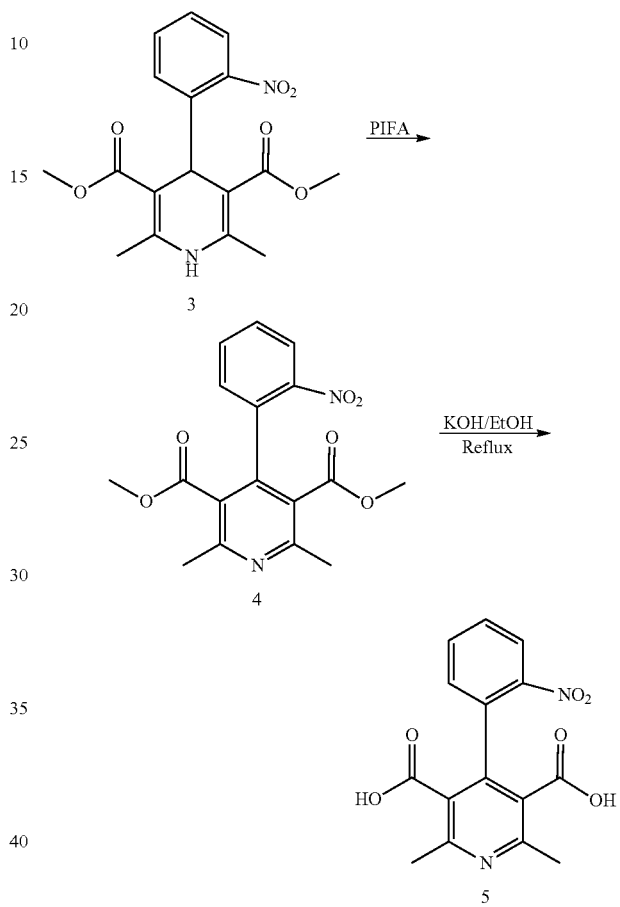

Synthesis of dimethyl 2,6-dimethyl-4-(2-nitrophenyl)pyridine-3,5-dicarboxylate (4): Nifepidine (3) is used as the starting material of said synthesis.

After nifepidine is dissolved in 1 g (2.89 mmol) 25 mL $CH_2Cl_2$ (Dichloromethane), 1.37 g (3.18 mmol) PIFA ((Bis(trifluoroacetoxy)iodo)benzene) is added. The mixture is stirred at room temperature for 12 hours. Crude product is washed with water (3×20) and the organic phase is dried over $Na_2SO_4$. The solvent of the organic phase is removed under vacuum. Oxidation product is crystallized over hexane. (900 mg, 90%).

Synthesis of 2,6-dimethyl-4-(2-nitrophenyl)pyridine-3,5-dicarboxylic acid (5): Dimethyl 2,6-dimethyl-4-(2-nitrophenyl)pyridine-3,5-dicarboxylate (4) obtained in the previous step is used as the starting material of said synthesis.

After dissolving dimethyl 2,6-dimethyl-4-(2-nitrophenyl)pyridine-3,5-dicarboxylate in 900 mg (2.61 mmol) 15 mL ethanol and 15 mL $H_2O$, 733 mg (13.07 mmol) KOH is added. The reaction is boiled at 80° C. for 16 hours. After the reaction is brought to room temperature, its solvent is removed under vacuum. Afterwards, it is dissolved in 30 mL water, and 0.1 M HCl is added to adjust the pH to 2, and it is kept at 2° C. for 12 hours. Obtained crystals are left to drying after filtering. 50 mg (66%) pure product is obtained.

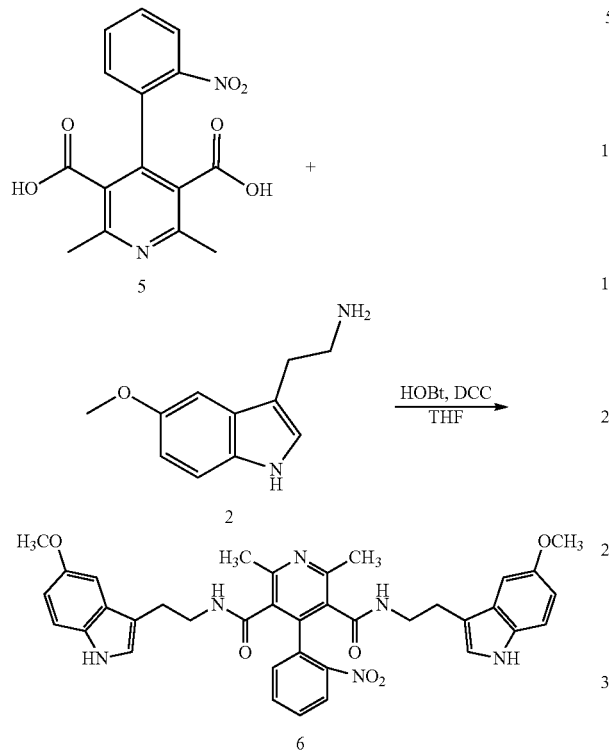

Synthesis of $N^3,N^5$-bis(2-(5-methoxy-1H-indol-3-yl)ethyl)-2,6-dimethyl-4-(2-nitrophenyl)pyridine-3,5-dicarboxamide (6): Dimethyl 2,6-dimethyl-4-(2-nitrophenyl)pyridine-3,5-dicarboxylate (4) obtained in the previous step and 5-methoxytryptamine (2) obtained in the first step are used as the starting materials of said synthesis.

After dissolving 2,6-dimethyl-4-(2-nitrophenyl)pyridine-3,5-dicarboxylic acid in 550 mg (1.74 mmol) 10 mL THF (Tetrahydrofuran), HOBt (1-Hydroxybenzotriazole hydrate) 470 mg (3.488 mmol) is added and mixed for 10 minutes. Subsequently, 661 mg (3.48 mmol) DCC is added to the reaction mixture and stirred for 30 minutes (1st mixture).

In another reaction balloon, after dissolving 5-methoxytryptamine (2) in 661 mg (3.48 mmol) 10 mL THF, $Et_3N$ (Triethylamine) 485 µL (3.48 mmol) is added and stirred for 30 minutes (2nd mixture).

The resulting 2nd mixture is added to the 1st mixture, and stirred at room temperature for 12 hours. Afterwards, the DCU formed is filtered through filter paper, and the solvent is removed under vacuum. Crude product is firstly washed with $NaHCO_3$ (3×30 mL); and then with 5% $KHSO_4$ (3×30 mL) and finally with water (3×30 mL), and the organic phase is dried over $Na_2SO_4$. The solvent of the organic phase is removed under vacuum. The resulting crude product is purified through silica gel column with $MeOH/CH_2Cl_2$ (5%) and 400 mg (35%) yellow solid product is obtained.

The active regions of the compound of the invention are marked as shown below. A characteristic of the invention is blocking the $Ca^{++}$ channels together with the dihydropyridine group and by showing antioxidant effect with the help of the carbonyl group, providing protective effect against the glutamate toxicity of the cell.

The Raw Materials Used During Synthesis of the Molecule of the Invention with the Above Given Operation Steps and their % Ratios;

| Raw material | Preferred amount by weight (%) |
| --- | --- |
| Nifepidine | 20 |
| Melatonin | 20 |
| $H_2SO_4$ | 1.331 |
| NaOH | 2 |
| Ethyl acetate | 4 |
| $Na_2SO_4$ | 4 |
| PIFA | 1.37 |
| $H_2O$ | 15 |
| Hexane | 2 |
| Ethanol | 6 |
| KOH | 0.733 |
| HCl 0.1M | 6 |
| THF | 4 |
| HOBt | 0.470 |
| DCC | 0.661 |
| $Et_3N$ | 0.485 |
| $NaHCO_3$ | 4 |
| 5% $KHSO_4$ | 8 |

The medicine according to the invention can be administered orally or in the form of an IV sustained release implant.

The invention claimed is:
1. A method for production of $N^3,N^5$-bis(2-(5-methoxy-1H-indol-3-yl)ethyl)-2,6-dimethyl-4-(2-nitrophenyl)pyridine-3,5-dicarboxamide molecule represented by the following formula:

so as to eliminate neurotoxicity observed in neuron cells, the method comprising:
   synthesizing 5-methoxytryptamine, by the steps of:
      boiling melatonin in a $H_2SO_4$ solution;
      adding NaOH until the medium becomes alkaline after the reaction is brought to room temperature;
      subsequently washing with ethyl acetate and drying an organic phase over $NaSO_4$; and
      removing a solvent thereof under vacuum;
   synthesizing dimethyl 2,6-dimethyl-4-(2-nitrophenyl)pyridine-3,5-dicarboxylate by the steps of:
      adding PIFA after dissolving nifepidine in $CH_2Cl_2$;
      stirring a resulting mixture at room temperature;
      washing a crude product with water and drying an organic phase thereof over $NaSO_4$,
      removing an organic phase solvent under vacuum; and
      crystallizing an oxidation product over hexane;

synthesizing 2,6-dimethyl-4-(2-nitrophenyl)pyridine-3,5-dicarboxylic acid by the steps of:
   adding KOH after dissolving dimethyl 2,6-dimethyl-4-(2-nitrophenyl)pyridine-3,5-dicarboxylate in ethanol and $H_2O$;
   boiling a reaction thereof at 80° C. for 16 hours;
   removing a solvent thereof under vacuum after the reaction is brought to room temperature;
   dissolving a remaining residue in water and adding HCl; and
   following filtering leaving resulting crystals to dry;
dissolving the synthesized 2,6-dimethyl-4-(2-nitrophenyl)pyridine-3,5-dicarboxylic acid in THF, and stirring following addition of HOBt;
obtaining a first mixture after addition of DCC to a resulting mixture and stirring;
dissolving synthesized 5-methoxytryptamine in THF and then obtaining a second mixture following addition of $Et_3N$ and mixing in another reactions vessel; and
adding the resulting second mixture to the first mixture and stirring.

2. The method for production of claim 1, further comprising:
   filtering a resulting mixture from the step of adding the resulting second mixture of the first mixture through a filter paper and removing a solvent thereof under vacuum;
   washing the crude product first with $NaHCO_3$ and then with 5% $KHSO_4$, and finally drying the organic phase over $Na_2SO_4$ with water;
   removing a solvent of the organic phase under vacuum; and
   purifying a resulting crude product through silica gel column via $MeOH/CH_2Cl_2$.

* * * * *